US00PP10833P

United States Patent [19]

Lim

[11] Patent Number: Plant 10,833

[45] Date of Patent: Mar. 23, 1999

[54] PEACH TREE NAMED 'WANGDO'

[76] Inventor: Jung-kyoung Lim, 637-1 Woulhari, Seomyun, Yunkikun, Chungnam, Rep. of Korea

[21] Appl. No.: 862,644

[22] Filed: May 23, 1997

[51] Int. Cl.[6] ..... A01H 5/00

[52] U.S. Cl. ..... Plt./42.1

[58] Field of Search ..... Plt./42.1, 40.1

[56] References Cited

FOREIGN PATENT DOCUMENTS 052872 2/1992 Rep. of Korea .

*Primary Examiner*—Howard J. Locker

*Attorney, Agent, or Firm*—Pepper Hamilton LLP

[57] ABSTRACT

A new and distinct variety of peach tree (*Prunus persica*) with the following combination of unique and desirable characteristics:

1. Heavy and regular production of fruit;
2. Production of very firm, white flesh fruit with good handling and shipping quality;
3. Fruit that will stay firm on the tree 10 to 17 days after maturity (shipping ripe);
4. Fruit with excellent flavor and eating quality;
5. Middle season maturity of white flesh fruit;
6. Fruit with an attractive red skin blush; and
7. Vigorous, half open growth habit.

2 Drawing Sheets

BACKGROUND OF VARIETY

In the country of origin, Republic of Korea, the tree of this disclosure is believed to have been derived from the commercial variety 'Yumyeong', and within the subspecies *dianthiflora* (Dipp.); and, originated in Seomyun, Yunkikun, Chungnam, Republic of Korea. The appropriate botanical classification for this tree is believed to be *Prunus persica*. This subject tree is believed to be exceptional in a number of characteristics and will offer a further option to commercial growers of stone fruits in terms of fruit having large to very large size, firm flesh, clingstone, sweet, attractively colored fruit which has a comparatively high capacity to withstand handling, shipping and storage. Having the additional desirable fruit characteristics of heavy production of fruit with an extensive surface blush of red coloration, an attractive shape and pleasant, sweet taste, and earlier than normal harvest for fruit of large to extra large size, this tree promises to be a valuable new variety to industry and commerce. This tree further has the advantage of being mid to late-season in blooming so that it is less susceptible to late frosts than other locally adapted tree varieties. I am not aware of varieties which offer a similar or comparable combination of characteristics.

ORIGIN OF THE VARIETY

The new tree was selected from among several thousand seedlings of the variety 'Yumyeong', which had been planted on my farm in Seomyun, Yunkikun, Chungnam, Korea. The seedling was discovered near a specimen of the noted apparent seed parent, which is a late season variety and which normally ripens between August 20 and September 10. My attention was drawn to this tree when I noticed that it was unusually precocious; producing two to three times more flowers than the parent 'Yumyeong' variety, and by having flowers of a much brighter color than the parent variety. With the recognition of these different characteristics, I allowed the tree to remain for further observation. Upon development and ripening of the fruit, it became clear to me that this tree showed promise due to its production of very high quality fruit of large to extra large size and unusual attractiveness. Based on these observations, I selected the variety for asexual reproduction and commercialization.

ASEXUAL REPRODUCTION OF THE VARIETY

Asexual reproduction of the new and distinct variety was performed by budding in my orchard located in Seomyun Yunkikun, Chungnam, Korea and shows that all characteristics run true to the original tree and are established and transmitted through succeeding propagations.

SUMMARY OF THE VARIETY

The present new and distinct variety of peach tree has been denominated 'Wangdo', and is of large size, vigorous half open growth and a regular and productive bearer of large, red skin, white flesh, clingstone fruit with a mild, sweet flavor with excellent eating and stock quality. The fruit is further characterized by having very firm flesh, the ability to hang on the tree 10 to 17 days after maturity (shipping ripe), having good handling and shipping quality, a pink skin ground color overspread with an attractive red blush and ripening in the middle maturity season, approximately 20 days after 'Changbang joseng', and 10 days before 'Yumyeong', both unpatented varieties, which are both widely planted in Korea.

DESCRIPTION OF THE PHOTOGRAPHS

Figure 1:
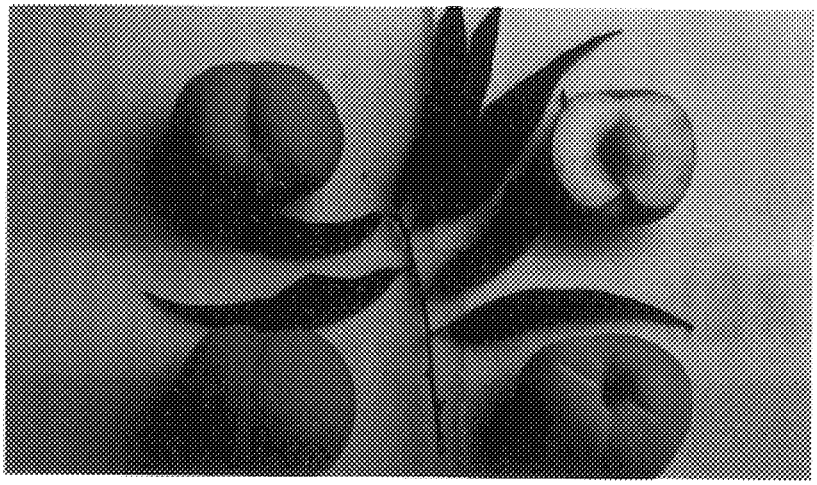
FIG. 1 shows typical specimens of the foliage and fruit of the new and distinct peach variety shortly after being picked (firm ripe); illustrating the upper and lower surface of the leaves, the exterior of the fruit, a fruit divided in its suture plane to reveal flesh coloration, pit cavity, and a stone remaining in place.
Figure 2:
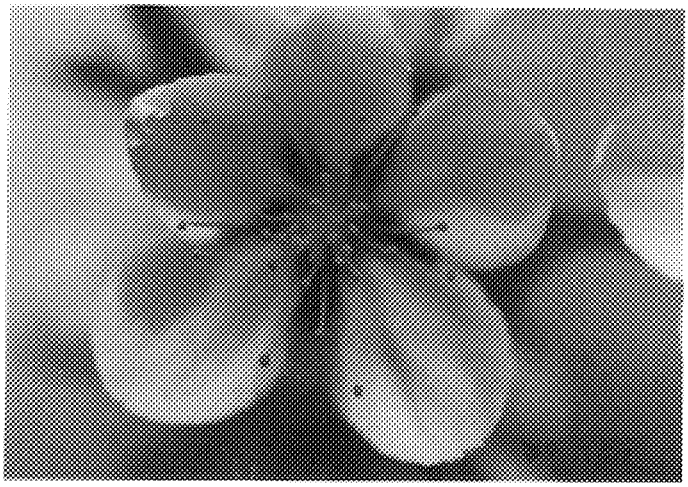
FIG. 2 depicts a flower of the peach tree 'Wangdo'.
Figure 3:
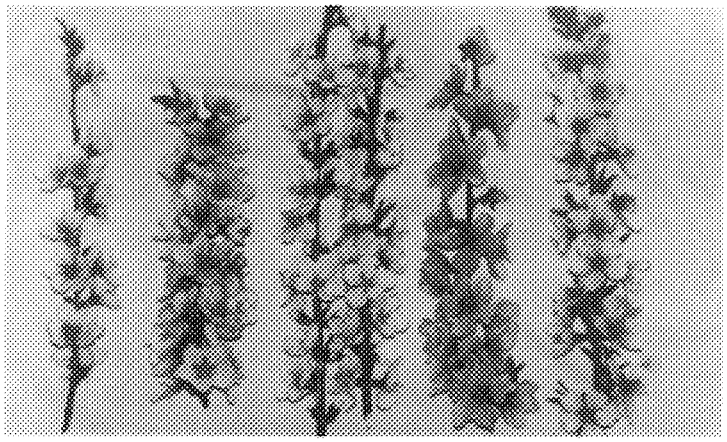
FIG. 3 depicts the blossoms of 'Yumyeong' (unpatented), 'Woulme' (unpatented), 'Baekyakdo' (the subject of copending U.S. plant patent application Ser. No. 08/862,645), 'Changbang joseng' (unpatented), and 'Wangdo', from left to right.
Figure 4:
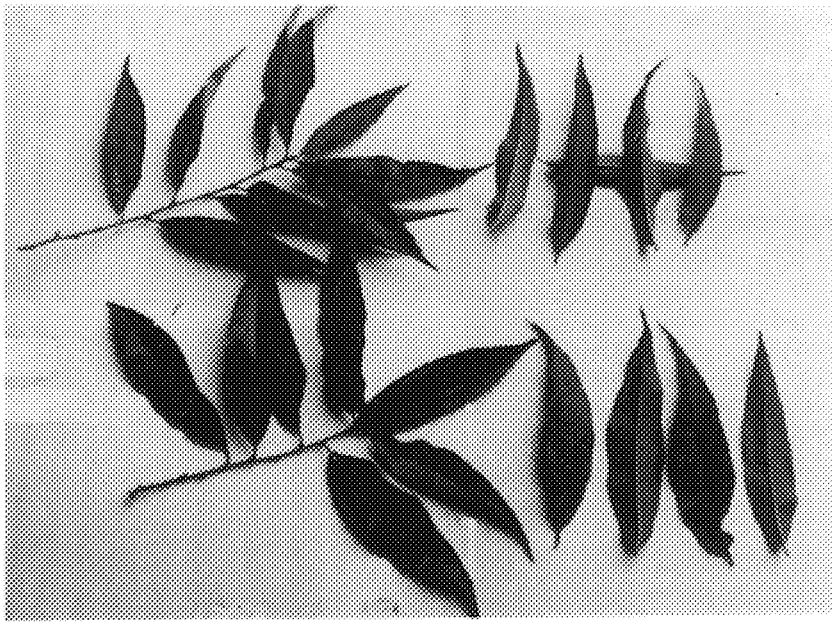
FIG. 4 depicts typical leaves from 'Wangdo' (above) and 'Woulme' (below), the leaf shape of 'Wangdo' being substantially narrower.

The colors depicted are as true as is reasonably possible to attain in color reproductions of this type, and the color designations set forth in the specification are believed to be accurate.

DESCRIPTION OF THE VARIETY

The following is a detailed botanical description of the new and distinct variety of peach tree, its flowers, fruit and foliage as based on observations of the specimen grown in my orchard located Seomyun Yunkikun Chungnam, Korea, with color terminology (except those in common terms) in accordance with PANTON® Professional Color System Selector (Pantone, Inc., 1984, 1990).

Tree:
- *Size.*—Large.
- *Vigor.*—Vigorous. Having terminal growth of 1.5 meters to 2 meters per year, in Chungnam, Korea.
- *Form.*—Grows 1.5 to 2 meters every year from the first to the third year, with the trunk terminating at 3 to 3.5 meters in height, and the branches extending from 1.5 2 meters per year at an upward angle of 40 to 60 degrees. More highly branched than the parent 'Yumyeong' variety. Requires about 60% pruning in order to obtain large fruit.
- *Production.*—Productive.
- *Bearing.*—Regular.
- *Density.*—Medium dense.

Trunk:
- *Size.*—Medium to stocky.
- *Texture.*—Smooth.
- *Color.*—Brown (18-1235) to (18-1137).

Branches:
- *Size.*—Medium.
- *Texture.*—Varies from smooth to medium rough with maturity.
- *Lenticels.*—Medium size. Medium number.
- *Color.*—Brown to light green (18-1031) to (18-1130).

Leaves:
- *Size.*—Medium to large. Narrow and long. Average length — 15 to 16.5 cm. Average width — 2.2 to 2.5 cm.
- *Form.*—Lanceolate-pointed.
- *Texture.*—Smooth.
- *Thickness.*—Medium.
- *Margin.*—Crenate.
- *Petiole.*—Medium length. Medium thickness.
- *Glands.*—Reniform. Number varies from 0 to 5. Average number 2. Located on base of leaf blade and upper portion of petiole.
- *Color.*—Upper surface green to dark green (18-01117) to (18-0322). Lower surface dull green to grayish green (17-6319) to (17-0119).

Flower buds:
- *Size.*—Large.
- *Form.*—Plump.
- *Length.*—Medium.
- *Pubescence.*—Pubescent.

Flowers:
- *Size.*—Medium — non-showy.
- *Blooming period.*—Apr. 15, 1995 to Apr. 25, 1995. Varies slightly due to climatic conditions.
- *Color.*—Pink.
- *Pollen.*—Much.

The tree is not self-fertile.

Fruit:
- *Maturity when described.*—Firm ripe.
- *Date of first picking.*—Aug. 8, 1995.
- *Date of last picking.*—Aug. 25, 1995.
- *Size.*—Large. Average diameter axially 8.5 to 11 cm. Average transversely in suture plane 7.5 to 10 cm.
- *Form.*—Globose — slight tip at apex and slightly flattended on stem end.
- *Suture.*—Shallow but pronounced, extends from base to apex.
- *Ventral surface.*—Nearly rounded, very slightly lipped.
- *Apex.*—Varies from rounded to slight pistil point.
- *Base.*—Retuse.
- *Cavity.*—Rounded to slightly elongated in suture plane. Average depth — 1.3 cm. Average breadth 1.9 cm.

Skin:
- *Thickness.*—Medium.
- *Texture.*—Tenacious to flesh.
- *Tendency to crack.*—None.
- *Down.*—Moderate amount, short to very short in length.
- *Color.*—Pink (17-1553) to (17-1545). Overspread with light red to yellowish pink (13-1012) to (12-0913).

Flesh:
- *Texture.*—Very firm.
- *Ripens.*—Evenly.
- *Fibers.*—Small, tender.
- *Juice.*—Moderate.
- *Flavor.*—Excellent, mild, very sweet.
- *Aroma.*—Moderate.
- *Eating quality.*—Excellent.
- *Amygdalin.*—Undetected.
- *Color.*—White to milky white (no Pantone number) to (11-0507), Pit cavity red to light red (15-2217) to (14-23118). Color extends from pit cavity outward into flesh, heavier near apex.

Stone:
- *Type.*—Clingstone.
- *Size.*—Large. Average length 2.5 cm. Average width 2.3 cm. Average thickness 1.5 cm.
- *Form.*—Ovoid.
- *Base.*—Mostly straight-some rounded.
- *Apex.*—Acuminate.
- *Sides.*—Equal.
- *Surface.*—Irregularly furrowed toward apex, ridges usually founded, pitted toward base.
- *Tendency to split.*—None.
- *Color.*—Brown to reddish brown (18-1540) to (19-1540).

Use: Dessert.
- *Market.*—Local and long distance.

Keeping quality: Very good.
Shipping quality: Very good.

The new and distinct variety of peach tree, its flowers, foliage and fruit described above may vary in slight detail due to variations in climate, soil conditions and cultural practices under which the variety may be grown. The botanical description above is that of the variety grown under the ecological conditions prevailing near Seomyun Yunkikun Chungnam, Korea.

I claim:

1. A new and distinct variety of peach tree, substantially as illustrated and described, characterized by its large size, vigorous, half open growth and being a regular and productive bearer of large, middle season maturing, white flesh, clingstone fruit with excellent flavor and eating quality; the fruit is further characterized by having very firm flesh, good handling and shipping quality and having a pink skin ground color overspread with an attractive red blush.

* * * * *

UNITED STATES PATENT AND TRADEMARK OFFICE

CERTIFICATE OF CORRECTION

PATENT NO. : PP 10,833
DATED : March 23, 1995
INVENTOR(S) : Joon-Kyong IM

It is certified that error appears in the above-identified patent and that said Letters Patent is hereby corrected as shown below:

Description of the Variety:

Column 3,
7th line from the bottom, delete "not".-

Signed and Sealed this

Twenty-eighth Day of August, 2001

*Attest:*

Nicholas P. Godici

*Attesting Officer*

NICHOLAS P. GODICI
*Acting Director of the United States Patent and Trademark Office*